(12) United States Patent
Bolckmans et al.

(10) Patent No.: US 11,026,409 B2
(45) Date of Patent: ***Jun. 8, 2021

(54) *PHYTOSEIID* PREDATORY MITE RELEASING SYSTEM AND METHOD FOR PRODUCTION

(71) Applicant: Koppert B.V., Berkel en Rodenrijs (NL)

(72) Inventors: Karel Jozef Florent Bolckmans, Hoogstraten (BE); Yvonne Maria Van Houten, Naaldwijk (NL); Adelmar Emmanuel Van Baal, Delft (NL); Arno Theodoor Stam, Schiedam (NL)

(73) Assignee: Koppert B.V., Berkel en Rodenrijs (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/608,713

(22) Filed: May 30, 2017

(65) Prior Publication Data
US 2017/0325430 A1 Nov. 16, 2017

Related U.S. Application Data

(63) Continuation of application No. 14/345,606, filed as application No. PCT/NL2012/050663 on Sep. 19, 2012, now Pat. No. 9,693,540.

(30) Foreign Application Priority Data

Sep. 20, 2011 (NL) ..................................... 1039058

(51) Int. Cl.
*A01K 67/033* (2006.01)
*A01K 1/00* (2006.01)
*A01N 63/00* (2020.01)

(52) U.S. Cl.
CPC .............. *A01K 67/033* (2013.01); *A01K 1/00* (2013.01); *A01N 63/00* (2013.01)

(58) Field of Classification Search
None
See application file for complete search history.

(56) References Cited

U.S. PATENT DOCUMENTS

| 7,947,269 | B2 | 5/2011 | Bolckmans et al. |
| 8,097,248 | B2 | 1/2012 | Bolckmans et al. |
| 8,957,279 | B2 | 2/2015 | Bolckmans et al. |
| 2009/0205057 | A1* | 8/2009 | Bolckmans .......... A01K 67/033 800/8 |
| 2010/0119645 | A1* | 5/2010 | Fidgett .................. A01N 63/00 426/2 |

FOREIGN PATENT DOCUMENTS

| WO | WO2007075081 A1 | 7/2007 |
| WO | WO2008015393 A2 | 2/2008 |

OTHER PUBLICATIONS

Demite et al , Zootaxa, 3795(5):571-577 (2014) (Year: 2014).*
Ryu et al., Kor. J. Appl. Entomol., 50(40):295-299 (2011) (Year: 2011).*
Beerling et al,. Proc. Exper. Appl. Entomol., 4:199-204 (1993) (Year: 1993).*
Chmielewski, Fagopyrurn, 18:61-64 (2001) (Year: 2001).*
Hessein et al., Cali. Agri., Nov. 19-Dec. 21, 1990 (Year: 1990).*
Yasui et al., 9(3):517-524 (1996) (Year: 1996).*
Badii et al., Prey stage preference and functional response of Euseius hibisci to Tetranychus urticae (Acari: Phytoseiidae, Tetranychidae), Exp Appl Acarol. 2004;34(3-4):263-73.

* cited by examiner

*Primary Examiner* — Thomas J. Visone
(74) *Attorney, Agent, or Firm* — Bret E. Field; Bozicevic, Field & Francis LLP

(57) ABSTRACT

The present invention in general relates to the field of biological crop protection by use of phytoseiid predatory mites. More particularly the present invention relates to a system for releasing a phytoseiid predatory mite in a crop and novel uses of host mites in such phytoseiid predatory mite releasing system. The phytoseiid predatory mite releasing system according to the invention and the uses according to the invention are characterised by the selection a host mite species having an intrinsic growth rate ($r_m$) of <0.28.

9 Claims, 1 Drawing Sheet

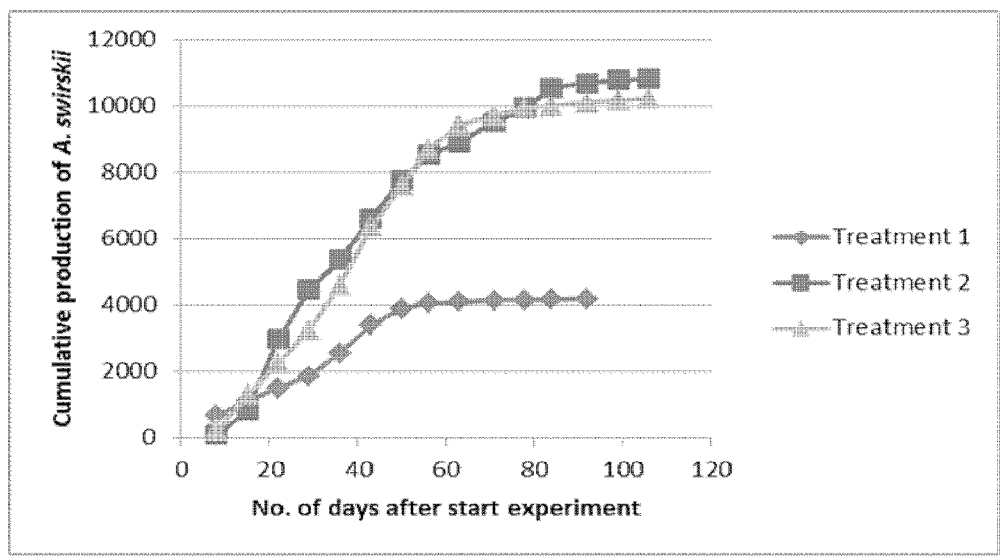

PHYTOSEIID PREDATORY MITE RELEASING SYSTEM AND METHOD FOR PRODUCTION

CROSS-REFERENCE TO RELATED APPLICATIONS

This application is a continuation of U.S. patent application Ser. No. 14/345,606 filed Mar. 18, 2014, now issued as U.S. Pat. No. 9,693,540, which application is a 371 application of PCT/NL2012/050663 filed Sep. 19, 2012, which application claims priority to Dutch Application No. NL1039058 filed Sep. 20, 2011, all of which are incorporated by reference in their entirety.

The present invention in general relates to the field of biological crop protection by use of phytoseiid predatory mites. More particularly the present invention relates to a system for releasing a phytoseiid predatory mite in a crop and novel uses of host mites in such phytoseiid predatory mite releasing system.

The use of phytoseiid predatory mites for biological crop protection is becoming increasingly popular in agriculture and horticulture. Currently phytoseiid predators are employed to combat pests such as phytophagous mites, *thrips* and whiteflies. One of the driving forces behind this popularity is the availability of releasing systems for those phytoseiid predators that are used as a crop protection tool.

The current most efficient phytoseiid mite releasing systems are of the sachet type disclosed in GB 2 393 890. Such a releasing system comprises a container holding a reproducing population of a phytoseiid predator species, a reproducing population of a suitable host mite species (as a food source for the phytoseiid predator) and a food source for the host mite. Due to population development of the phytoseiid predator on the host mite and population development of the host mite on its food source, a system capable of prolonged release of the phytoseiid predator is created. In practice the prolonged release of the phytoseiid predatory is limited to about 3 to 6 weeks. Since the development of the phytoseiid mite releasing sachet system of GB 2 393 890, there have been major developments in respect of the availability of additional hosts for phytoseiid predators. Many of these newly available hosts are factitious hosts. Factitious host are hosts uncommon to the natural habitat of the phytoseiid mites viz. the phyllosphere. For example reference may be made to the international applications of Koppert B. V., WO2006/057552, WO2006/071107 and WO2007/075081. In addition WO2008/015393, WO2008/104807 and EP2232986 disclose additional combinations of phytoseiid predators and host mites.

Despite these developments in phytoseiid predator releasing systems in the past years, the phytoseiid predatory releasing activity of these systems is still limited to about 3 to 6 weeks. During this period the cumulative production of phytoseiid predators of the present releasing systems is limited to about 300 to 400 phytoseiid individuals per gram carrier contained in the releasing system.

SUMMARY

Research of the inventors of the present invention has shown that careful selection of hosts mites having certain special characteristics results in phytoseiid predators releasing systems having an improved performance in respect of duration of phytoseiid predator release and/or cumulative number of phytoseiid predators released.

The special characteristics of the host mite that result in the surprising effect relate to its intrinsic growth rate ($r_m$). It has now surprisingly been found that the use of a host mite having an intrinsic growth rate ($r_m$) of <0.28 can result in a phytoseiid predatory mite releasing system having phyoseiid predatory mite releasing activity of longer than 6 weeks (in particular longer than 7 weeks) and/or a cumulative number of phytoseiid predators produced of over 400 pytoseiid individuals per gram carrier during the life-time of the releasing system.

The fact that a host mite having an intrinsic growth rate ($r_m$) of <0.28 can result in a phytoseiid predatory mite releasing system having phyoseiid predatory mite releasing activity of longer than 6 weeks and/or a cumulative number of phytoseiid predators produced of over 400/gram carrier has not been recorded in the prior art.

The invention therefore, according to a first aspect, relates to a phytoseiid predatory mite releasing system having phytoseiid predatory mite releasing activity of at least 7 weeks and/or having a cumulative number of phytoseiid predators produced of over 400/gram carrier, comprising:
  a population of the phytoseiid predatory mite;
  a food source for the individuals of the phytoseiid predatory mite, comprising a population of a host mite having an intrinsic growth rate ($r_m$) of <0.28.

The phytoseiid predatory mite releasing system may be of any suitable type. In general the mite releasing system will comprise a container suitable for holding the individuals of the phytoseiid predatory mite and individuals of the host mite. The container comprises an opening and/or means for creating an exit opening for mobile stages of the phytoseiid predatory mite. Releasing systems of this type are known to the skilled person and various products are commercially available on the market, e.g. the Swirski-Mite® product of Koppert B. V. and other sachet-type releasing systems. In addition GB 2 393 890 discloses suitable types of releasing systems.

BRIEF DESCRIPTION OF THE FIG

FIG. 1 provides a graphical presentation of the average cumulative production of mite species as presented in table II of the Example.

DETAIL DESCRIPTION

The phytoseiid predatory mite releasing system comprises a population of a phytoseiid predatory mite. As is known to the skilled person phytoseiid predatory mites have their natural habitat on plants where they prey on pest organisms (insects and mites). They may be isolated from their natural habitats as described by de Moraes et al., 2004. Phytoseiid predatory mites that are particularly useful in the present invention may be selected from:
  the subfamily of the Amblyseiinae, such as from the Genus *Amblyseius*, e.g. *Amblyseius andersoni*, *Amblysieus aerialis*, *Amblyseius swirskii* or *Amblyseius largoensis*, from the genus *Euseius* e.g. *Euseius finlandicus*, *Euseius hibisci*, *Euseius ovalis*, *Euseius victoriensis*, *Euseius stipulatus*, *Euseius scutalis*, *Euseius tularensis*, *Euseius addoensis*, *Euseius concordis*, *Euseius ho* or *Euseius citri*, from the genus *Neoseiulus* e.g. *Neoseiulus barkeri*, *Neoseiulus californicus*, *Neoseiulus cucumeris*, *Neoseiulus longispinosus*, *Neoseiulus womersleyi*, *Neoseiulus idaeus*, *Neoseiulus anonymus* or *Neoseiulus fallacis*, from the genus *Typhlodromalus* e.g. *Typhlodromalus limonicus*,

*Typhlodromalus aripo* or *Typhlodromalus peregrinus* from the genus *Typhlodromips* e.g. *Typhlodromips montdorensis*;

the subfamily of the Typhlodrominae, such as from the genus *Galendromus* e.g. *Galendromus occidentalis*, from the genus *Typhlodromus* e.g. *Typhlodromus pyri, Typhlodromus doreenae* or *Typhlodromus athiasae*.

Preferably the phytoseiid predatory mite is selected from *Amblyseius swirskii, Amblysieus aerialis, Amblyseius andersoni, Neoseiulus barkeri, Neoseiulus californicus, Neoseiulus cucumeris, Neoseiulus fallacis* or *Typhlodromips montdorensis*.

The names of the phytoseiid mite subfamilies, genera and species as used in relation to this invention is as referred to in de Moraes, G. J. et al., 2004, unless otherwise stated.

The phytoseiid mite releasing system further comprises a food source suitable for the population development of the phytoseiid predatory mite population. This food source comprises a population of a host mite. The term host or host mite expresses that the mites selected as host are suitable prey for the phytoseiid predatory mite.

According to the invention the host mite has an intrinsic growth rate ($r_m$) of <0.28. The skilled person will know that the intrinsic growth rate is a population dynamics parameter reflecting a theoretical maximum rate of increase of a population per individual.

Experiments performed by the inventors have surprisingly shown that by using a host having an intrinsic growth rate ($r_m$) of <0.28, a phytoseiid predatory mite releasing system can be obtained which has prolonged phytoseiid releasing activity and/or has a higher cumulative phytoseiid mite release. Without wishing to be bound by this theory observations made by the inventors indicate that populations of hosts having a relatively low intrinsic growth rate ($r_m$) have a relatively low dispersal activity. Low dispersal activity of the host increases the chance that more individuals of the host mite remain in the releasing system, instead of migrating to outside the releasing system. This increases the probability that sufficient food is available to the phytoseiid predator in the releasing system during a longer time period.

According to the invention a host mite having an intrinsic growth rate ($r_m$) of <0.28 is used. The skilled person will know the meaning of the term intrinsic growth rate ($r_m$) and will know methods to establish $r_m$ values for host mites. Preferably such $r_m$ values are determined at 25° C. and 85% relative humidity (RH). Values $r_m$ for different species may for example also be obtained from various literature sources. Within the context of this invention an intrinsic growth rate ($r_m$) of <0.28 should be understood to mean an intrinsic growth rate ($r_m$) of 0.02-0.28, such as 0.28, 0.27, 0.26, 0.25, 0.24, 0.23, 0.22, 0.21, 0.20, 0.19, 0.18, 0.17, 0.16, 0.15, 0.16, 0.15, 0.14, 0.13, 0.12, 0.11, 0.10, 0.09, 0.08, 0.07, 0.06, 0.05, or 0.04. Preferably the intrinsic growth rate ($r_m$) has a value <0.25, such as <0.23, for example <0.20.

According to an embodiment of the invention the host mite having an intrinsic growth rate ($r_m$) of <0.28 is selected from *Lepidoglyphus destructor*. This mite and its use in rearing of phytoseiid predatory mites is disclosed in WO2007/075081. Experiments performed by the inventors have established the special effects of the use of this mite as a host for rearing phytoseiid predatory mites. The inventors of the invention have deduced that the special effects of this host are connected to its relatively low intrinsic growth rate ($r_m$) which positively reflects on its dispersal activity. The surprising effects shown for *Lepidoglyphus destructor* in connection to the prolonged phytoseiid releasing activity and higher cumulative phytoseiid mite release has not been reported in the art. Also the connection established by the inventors between these surprising effects and the intrinsic growth rate ($r_m$) of the host has not been reported in the art prior to the present invention. The $r_m$ value for *Lepidoglyphus destructor* is 0.18 (Stratil, Stratil & Kindle (1980))

On the basis of known knowledge about the intrinsic growth rate of other host mites additional selections of hosts suitable for use in the present invention can be made. For example for *Thyreophagus entomophagus* an $r_m$ value of 0.071 has been reported in the literature (Chmielewski, 1990). On the basis of this report this host may be selected for use in the present invention as a host mite having an intrinsic growth rate ($r_m$) of <0.28. The use of *Thyreophagus entomophagus*, as a host for rearing the phytoseiid predatory mite *Amblysieus swirskii* is disclosed in WO2008/015393. However this disclosure does not report the $r_m$ value of this mite, nor does it give any attention to the effects that may be obtained when selecting hosts with an $r_m$ value of <0.28.

The phytoseiid predatory mite releasing system further comprises a food source for the host mite. Selection of a suitable food source for the selected host mite is within the knowledge of the skilled person and may furthermore be derived from the disclosure of one or more of the following documents and the references cited therein: WO2006/057552, WO2006/071107, WO2007/075081, WO2008/015393.

According to a preferred embodiment, the host mite having an intrinsic growth rate ($r_m$) of <0.28 is a first host and the phytoseiid predatory mite releasing system, comprises a second host mite different from the first host mite. The addition of a further host mite suitable as a food source for the phytoseiid predatory mite may for example be beneficial in view of the fact that an improved population development of the phytoseiid predatory mite may be obtained.

For example, although the host mite having an intrinsic growth rate ($r_m$) of <0.28 may add to obtaining a prolonged phytoseiid predatory mite release from the system, it may not be the ideal host for the phytoseiid predatory mite in terms of population development rate. Combination with an additional host mite may improve the phytoseiid predator release in releasing systems during the early stages of deployment in a crop. In this way a fast initial phytoseiid predator release in the early stages after deployment of the releasing system may be combined with prolonged phytoseiid releasing activity.

Therefore, according to a further preferred embodiment the second host mite is selected, such that the phytoseiid predatory mite has improved population development on the second host than on the host mite having an intrinsic growth rate ($r_m$) of <0.28.

According to an alternative embodiment the second host mite has a higher intrinsic growth rate than the first host mite. The second host mite preferably has an intrinsic growth rate of at least 0.28, such as 0.28-0.45, for example 0.30, 0.31, 0.32, 0.33, 0.34, 0.35, 0.36, 0.37, 0.38, 0.39, 0.40, 0.41, 0.42, 0.43, 0.44.

A preferred host for selection as the second host is *Carpoglyphys lactis*. It should be noted that *Carpoglyphus lactis* is not a host mite having an intrinsic growth rate ($r_m$) of <0.28. Instead the reported $r_m$ value of this host is 0.29 (Chmielewski (1971)). In addition observations made by the inventors have classified this host as a host having relatively high dispersal behavior.

Specific combinations of phytoseiid predatory mites, host mites having an intrinsic growth rate ($r_m$) of <0.28 and optionally second host mites that are particularly contemplated within the present invention are presented in the table I below. It should specifically be noted that these combinations are contemplated within all aspects of the invention including the release system, the use of the host mite having an intrinsic growth rate ($r_m$) of <0.28 in manufacturing the release system and the method for manufacturing the release system.

TABLE I

| Phytoseiid predator | Host having $r_m$ < 0.28 | second host |
|---|---|---|
| Amblyseius swirskii | Lepidoglyphus destructor | None |
| Amblyseius swirskii | Lepidoglyphus destructor | Carpoglyphus lactis |
| Amblyseius swirskii | Thyreophagus entomophagus | None |
| Amblyseius swirskii | Thyreophagus entomophagus | Carpoglyphus lactis |
| Amblysieus aerialis | Lepidoglyphus destructor | None |
| Amblysieus aerialis | Lepidoglyphus destructor | Carpoglyphus lactis |
| Amblysieus aerialis | Thyreophagus entomophagus | None |
| Amblysieus aerialis | Thyreophagus entomophagus | Carpoglyphus lactis |
| Amblyseius andersoni | Lepidoglyphus destructor | None |
| Amblyseius andersoni | Lepidoglyphus destructor | Carpoglyphus lactis |
| Amblyseius andersoni | Thyreophagus entomophagus | None |
| Amblyseius andersoni | Thyreophagus entomophagus | Carpoglyphus lactis |
| Neoseiulus barkeri | Lepidoglyphus destructor | None |
| Neoseiulus barkeri | Lepidoglyphus destructor | Carpoglyphus lactis |
| Neoseiulus barkeri | Thyreophagus entomophagus | None |
| Neoseiulus barkeri | Thyreophagus entomophagus | Carpoglyphus lactis |
| Neoseiulus cucumeris | Lepidoglyphus destructor | None |
| Neoseiulus cucumeris | Lepidoglyphus destructor | Carpoglyphus lactis |
| Neoseiulus cucumeris | Thyreophagus entomophagus | None |
| Neoseiulus cucumeris | Thyreophagus entomophagus | Carpoglyphus lactis |
| Neoseiulus fallacis | Lepidoglyphus destructor | None |
| Neoseiulus fallacis | Lepidoglyphus destructor | Carpoglyphus lactis |
| Neoseiulus fallacis | Thyreophagus entomophagus | None |
| Neoseiulus fallacis | Thyreophagus entomophagus | Carpoglyphus lactis |
| Typhlodromips montdorensis | Lepidoglyphus destructor | None |
| Typhlodromips montdorensis | Lepidoglyphus destructor | Carpoglyphus lactis |
| Typhlodromips montdorensis | Thyreophagus entomophagus | None |
| Typhlodromips montdorensis | Thyreophagus entomophagus | Carpoglyphus lactis |

With the phytoseiid predatory mite releasing system according to the invention according to an embodiment a phytoseiid mite releasing activity of at least 7 weeks can be obtained. The phytoseiid mite releasing systems currently on the market have phytoseiid mite releasing activity of up to 4 to 6 weeks. Within the present invention at least 7 weeks includes, at least 8 weeks, at least 9 weeks, at least 10 weeks, at least 11 weeks. The period of at least 7 weeks may also be expressed in days as at least 49 days. Within the present invention at least 49 days includes 50-78 days such as, 51, 52, 53, 54, 55, 56, 57, 58, 59, 60, 61, 62, 63, 64, 65, 66, 67, 68, 69, 70, 71, 72, 73, 74, 75, 76 or 77 days.

According to another embodiment a cumulative phytoseiid mite releasing activity of at least 400 phytoseiid individuals per gram carrier can be obtained. The phytoseiid mite releasing systems currently on the market have a cumulative phytoseiid mite releasing activity which is limited to about 300 to 400 phytoseiid individuals per gram carrier. At least 400, should be construed to include 400-1000, such as 450, 500, 550, 600, 650, 700, 750, 800, 850, 900, 950, 1000.

The skilled person will be able to determine suitable amounts and ratio's for the phytoseiid predatory mite and the host. Examples of suitable ratio's may be derived from WO2006/057552, WO2006/071107, WO2007/075081 or WO2008/015393. Alternatively in the phytoseiid predator releasing system the ratio of individuals of the phytoseiid predatory mite species relative to the number of individuals of the host may be from about 1000:1, such as about 100:1. Alternatively the ratio of individuals of the phytoseiid predatory mite species relative to the number of individuals of the host may be from 1:1 to 1:100, e.g. 1:2 to 1:50, 1:2 to 40, 1:2 to 1:30. If a first and second host are used, they may be used in a different ratio's. It that case it may be beneficial to add a larger amount of the host having an intrinsic growth rate ($r_m$) of <0.28, relative to the second host.

The skilled person will understand that the phytoseiid release systems work optimal under conditions of 20-30° C., preferably 20-25° C. and a RH of 77%±10%, preferably 83-87% RH, most preferably 85% RH. Therefore it is most preferred to maintain the releasing system under such conditions during its use, especially at 20-25° C. and 83-87% RH.

The phytoseiid predator releasing system according to the invention may be used for controlling a crop pest. The crop pest may be selected from white flies, such as *Trialeurodes vaporariorum* or *Bemisia tabaci*; thrips, such as *Thrips tabaci* or *Frankliniella* spp., such as *Frankliniella occidentalis*; spider mites such as *Tetranychus* spp. such as *Tetranychus urticae, Teranychus evansi* and Teranychus *kanzawai* or *Panonychus* spp. such *Panonychus ulmi*; tarsonemid mites such as *Polyphagotarsonemus latus* or *Tarsonemus pallidus*; eriophyid mites such as *Aculops lycopersici*; mealybug crawlers such as from *Panonychus citri*; scale crawlers such as from *Aonidiella aurantii*.

The crop to be protected may be selected from (greenhouse) vegetable crops such as tomatoes (*Lycopersicon esculentum*), peppers (*Capsicum annuum*, eggplants (*Solanum melogena*), Curcubits (Cucurbitaceae) such as cucumbers (*Cucumis sativa*), melons (*Cucumis melo*), watermelons (*Citrullus lanatus*); soft fruit (such as strawberries (*Fragaria x ananassa*), raspberries (*Rubus ideaus*)), (greenhouse) ornamental crops (such as roses, gerberas, chrysanthemums), tree crops such as *Citrus* spp., almonds, banana's or open field crops such as cotton, corn.

A further aspect of the present invention is aimed at the use of a host mite having an intrinsic growth rate ($r_m$) of <0.28 for manufacturing a phytoseiid predatory mite releasing system having phytoseiid predatory mite releasing activity of at least 7 weeks and/or a cumulative production of phytoseiid predators of over 400 per gram carrier. As discussed above the phytoseiid predatory mite releasing system of the invention has utility in crop protection, in particular in horticulture. For this aspect of the invention similar preferred and alternative embodiments, as discussed in connection to the phytoseiid predatory release system, may be defined. The benefits of these preferred and alternative embodiments within this aspect of the invention will be evident from the discussion in connection to the phytoseiid predatory release system.

Yet a further aspect of the invention relates to a method for producing a phytoseiid predatory mite releasing system. The method comprises the steps of:
(A) selecting a phytoseiid predatory mite;
(B) rearing the phytoseiid predatory mite in a rearing composition comprising:
  a population of the phytoseiid predatory mite;
  a population of a rearing host mite;
  a food source for the rearing host mite;
(C) optionally, adding a population of an additional host mite to the rearing composition;
(D) providing a container suitable to hold the phytoseiid predatory mite, said container having an exit for mobile stages of the phytoseiid predatory mite;
(E) packing the rearing composition, optionally together with the additional host in the container.

This method is characterised in that for the rearing host and/or for the optional additional host, a host mite having an intrinsic growth rate $(r_m)$ of <0.28 is selected. With this method the phytoseiid predatory mite releasing system according to the invention may be produced.

In the method according to the invention a phytoseiid predatory mite is selected. The phytoseiid predatory mite may be any phytoseiid predatory mite. Phytoseiid predatory mites that are of particular interest of the present invention have already been discussed in connection to the releasing system of the invention. Preferably the phytoseiid predatory mite is selected from *Amblyseius swirskii, Amblysieus aerialis, Amblyseius andersoni, Neoseiulus barkeri, Neoseiulus californicus, Neoseiulus cucumeris, Neoseiulus fallacis* or *Typhlodromips montdorensis*.

In the method the phytoseiid predatory mite is reared in a rearing composition comprising:
  a population of the phytoseiid predatory mite;
  a population of a rearing host mite;
  a food source for the rearing host mite.

Such rearing may be performed according to procedures known to the skilled person, for example procedures known from WO2006/057552, WO2006/071107, WO2007/075081, WO2008/015393 or the references cited in any of these documents.

In the method according to the invention optionally, a population of an additional host mite is added to the rearing composition. When added the additional host preferably is distributed homogenously through the rearing composition. Details of the optional additional host mite will be discussed in more detail below.

In the method according to the invention providing a container suitable to hold the phytoseiid predatory mite is provided. Said container having an exit for mobile stages of the phytoseiid predatory mite. Alternatively the container is provided with means suitable for creating an exit opening for mobile stages of the phytoseiid predatory mite. The technical details of the container have been discussed above in connection to the releasing system according to the invention.

The rearing composition is packed in the container with the use of procedures know to the skilled person. When added to the rearing composition the optional additional host is packed in the container together with the rearing composition.

The method according to the invention is characterised in that, a host mite having an intrinsic growth rate $(r_m)$ of <0.28 is selected. This host having an intrinsic growth rate $(r_m)$ of <0.28 may be the rearing host or alternatively, in case an additional host is added, may also be the additional host. Preferably the host mite having an intrinsic growth rate $(r_m)$ of <0.28 is the additional host. In this case the rearing host is the second host as discussed in relation to the mite releasing system of the invention. Possible selections for and details of both the host mite having an intrinsic growth rate $(r_m)$ of <0.28 and the additional host have been discussed above in relation to the mite releasing system of the invention.

Also in respect of the method of the invention preferred and alternative embodiments, similar to those discussed in connection to the phytoseiid predatory release system, may be defined. The benefits of these preferred and alternative embodiments within the context of the method of the invention will be evident to the skilled person in view of the discussion in connection to the phytoseiid predatory release system.

The invention will now be discussed with reference to the following example.

Example

Two stock rearing systems of *A. swirskii* were maintained at Koppert: (I) *A. swirskii* on host mite *C. lactis* and (II) *A. swirskii* on host mite *L. destructor*. Using these two stock rearing systems, three different rearing compositions were prepared:
1. A carrier material of humidified bran and nutrients containing approx. 100 *A. swirskii* and 300 *C. lactis* per gram (standardized slow release system of Koppert Biological Systems).
2. A carrier material of humidified bran and nutrients containing approx. 50 *A. swirskii* and 1000 *L. destructor* per gram.
3. A carrier material of humidified bran and nutrients containing approx. 50 *A. swirskii,* 300 *C. lactis* and 1000 *L. destructor* per gram.

From each composition, 10 grams were poured (in duplo) into glass jars (three treatments×a duplo=totally 6 jars). Each glass jar was placed separately in a plastic bucket (10 liters) in a layer (2 cm deep) of saturated sodium chloride solution. The buckets were firmly closed with a non-aerating plastic lid. The salt solution provides an ambient relative humidity of 75%. Buckets were placed in a climate room at 21 degrees Celsius.

During the forthcoming week, mites (predatory mites and prey mites) escape the jars and drown in the salt solution. Once a week all glass jars were transferred to new, clean, plastic buckets with a new saturated salt solution. The number of escaped mites (or production of the release system) in the used buckets was assessed using known counting methods using a grid and binoculars. Half-way the time interval in between each measurement, lids from buckets were opened and closed to allow aeration.

Approximately every seven days this procedure was repeated until escape (production) of predatory mites decreased significantly.

The average cumulative production of all three mite species in of all three treatments is presented in the table II below. Graphical presentation of the date is presented in FIG. 1.

TABLE II

| | Treatment 1 | | | Treatment 2 | | | Treatment 3 | | |
|---|---|---|---|---|---|---|---|---|---|
| Day | A. swirskii | C. lactis | L. destructor | A. swirskii | C. lactis | L. destructor | A. swirskii | C. lactis | L. destructor |
| 8 | 692 | 1142 | 0 | 103 | 0 | 290 | 207 | 4933 | 0 |
| 15 | 1114 | 2101 | 0 | 835 | 0 | 802 | 1300 | 31222 | 0 |
| 22 | 1503 | 2677 | 0 | 2972 | 0 | 1550 | 2253 | 67167 | 124 |
| 29 | 1865 | 2824 | 0 | 4466 | 0 | 4483 | 3249 | 68746 | 920 |
| 36 | 2553 | 27301 | 0 | 5376 | 0 | 10782 | 4581 | 69923 | 1669 |
| 43 | 3417 | 28378 | 0 | 6626 | 0 | 21162 | 6345 | 71444 | 15661 |
| 50 | 3906 | 28685 | 0 | 7771 | 0 | 30499 | 7577 | 71600 | 20315 |
| 56 | 4064 | 28835 | 0 | 8520 | 0 | 35355 | 8689 | 71758 | 23593 |
| 63 | 4107 | 28997 | 0 | 8916 | 0 | 36047 | 9423 | 72022 | 26438 |
| 71 | 4145 | 29101 | 0 | 9501 | 0 | 37604 | 9711 | 72095 | 29563 |
| 78 | 4159 | 29366 | 0 | 9941 | 0 | 39046 | 9922 | 72112 | 32332 |
| 84 | 4167 | 29542 | 0 | 10540 | 0 | 39594 | 9992 | 72161 | 32803 |
| 92 | 4181 | 29774 | 0 | 10684 | 0 | 39931 | 10099 | 72161 | 35027 |
| 99 | | | | 10786 | 0 | 40297 | 10166 | 72161 | 36777 |
| 106 | | | | 10808 | 0 | 40393 | 10219 | 72206 | 36837 |

The data shows that treatments 1 and 3, both containing *C. lactis*, start producing predatory mites more quickly. Treatments 2 and 3, both containing *L. destructor*, produce significantly more predatory mites, and are more long-lasting (despite the lower start concentration of *A. swirskii*). From this data it is clear that treatments 2 and 3 perform better with respect to (1) cumulative production, (2) average production per week and (3) longevity of the system.

REFERENCES

De Moraes, G. J., McMurtry, J. A., Denmark, H. A. & Campos, C. B., 2004. A revised catalog of the mite family Phytoseiidae. Magnolia Press Auckland New Zealand 494 pp.

Chmielewski, W., 1971. Morfologia, biologia i ekologia *Carpoglyphus lactis* (L., 1758) (Glycyphagidae, Acarina), Prace-Naukowe-Instytutu-Ochrony-Roslin. 1971, publ. 1972, 13: 2, 63-166.

Chmielewski, W., 1990. Bio Ekologia I Rozwój poplacji *Thyreophagus entomophagus* (Lab.) (Acarida, Acaridae-rozkruszka znajdowanego w ulach pszczelich/Bio ecology and population development of *Thyreophagus*. pszczelnicze zeszyty naukowe 31-42.

Stratil, H. U., H. H. Stratil & W. Knülle., 1980. Untersuchungen über die spezifische Vermehrungsrate von Populationen der im Lagergetreide lebenden Milbe *Glycyphagus destructor* (Schrank, 1781) bei verschiedenen Temperatur- and Luftfeuchtebedingungen.

The invention claimed is:

1. A composition for releasing Phytoseiid predatory mites, the composition comprising:
   a population of the Phytoseiid predatory mite, wherein the Phytoseiid predatory mite is selected from *Amblyseius swirskii*, and *Neoseiulus cucumeris*;
   a food source for the individuals of the Phytoseiid predatory mite population, comprising:
      a population of a first factitious host mite that is a factitious host for the Phytoseiid predatory mite, wherein the first factitious host is *Lepidoglyphus destructor*; and
      a population of a second factitious host mite that is a factitious host for the Phytoseiid predatory mite, wherein the second factitious host is *Carpoglyphus lactis*; and
   a carrier comprising a food source for the host mites.

2. The composition according to claim 1, wherein the Phytoseiid predatory mite is *Neoseiulus cucumeris*.

3. The composition of claim 1, wherein the Phytoseiid predatory mite is *Amblyseius swirskii*.

4. The composition of claim 1, wherein the carrier comprises humidified bran and nutrients.

5. The composition of claim 1, wherein the carrier is selected from the group consisting of wheat bran, buckwheat husks, rice husks, saw dust, corn cob, and grits.

6. The composition of claim 1, wherein the food source for the host mites comprises sugar.

7. The composition of claim 6, wherein the sugar is selected from the group consisting of allose, altose, dextrose, glucose, sucrose, mannose, gulose, idose, galactose, talose, fructose, saccharose, lactose, and arabinose.

8. The composition of claim 1, wherein the food source for the host mites is selected from the group consisting of bran, rolled oats, corn grits, gram flour, buckwheat flour, cereal flours, dried fruit, jam, dried insects, and poultry meal.

9. A method for controlling a crop pest; the method comprising administering a composition according to claim 1 to a crop to control the crop pest.

* * * * *